(12) United States Patent
Wood et al.

(10) Patent No.: US 6,826,537 B1
(45) Date of Patent: Nov. 30, 2004

(54) CARDLESS METHOD FOR REDUCING FRAUD IN GOVERNMENT HEALTHCARE PROGRAMS

(76) Inventors: Richard Glee Wood, 4627 Cashel Cir., Houston, TX (US) 77069; Wesley Jack White, Jr., 6219 Squires Ct., Spring, TX (US) 77389

(*) Notice: Subject to any disclaimer, the term of this patent is extended or adjusted under 35 U.S.C. 154(b) by 0 days.

(21) Appl. No.: 10/443,189

(22) Filed: May 22, 2003

Related U.S. Application Data

(63) Continuation-in-part of application No. 10/428,609, filed on May 2, 2003.
(60) Provisional application No. 60/461,226, filed on Apr. 8, 2003, and provisional application No. 60/461,225, filed on Apr. 8, 2003.

(51) Int. Cl.[7] .............................................. G06F 17/60
(52) U.S. Cl. ............................................... 705/4; 705/2
(58) Field of Search ........................... 705/1–4; 283/54

(56) References Cited

U.S. PATENT DOCUMENTS

| | | | | |
|---|---|---|---|---|
| 5,884,271 A | * | 3/1999 | Pitroda ............................ | 705/1 |
| 6,011,858 A | * | 1/2000 | Stock et al. ................. | 382/115 |
| 6,012,035 A | * | 1/2000 | Freeman et al. ............... | 705/2 |
| 6,163,770 A | | 12/2000 | Gamble .......................... | 705/4 |
| 6,208,973 B1 | * | 3/2001 | Boyer et al. .................... | 705/2 |

FOREIGN PATENT DOCUMENTS

WO    WO 200039714 A1 * 7/2000 ........... G06F/17/30

OTHER PUBLICATIONS

Eiland, "A Bill to be Entitled an Act." Acts of the 75th Legislature, Regular Session, 1997.

Ogden, "A Bill to be Entitled an Act." Acts of the 78th Legislature, Regular Session, 2003.

"Texas Senate Special Committee on Prompt Payment of Health Care Providers." Interim Report to the 78th Legislature, Nov. 2002.

Rehnquist, Janet. "Improper Fiscal Year 2002 Medicare Fee–for–Service Payments," Jan. 8, 2003 (A17–02–02202).

\* cited by examiner

*Primary Examiner*—Joseph Thomas
*Assistant Examiner*—Christopher L Gilligan
(74) *Attorney, Agent, or Firm*—Wendy Buskop; Buskop Law Group, P.C.

(57) ABSTRACT

A method reducing fraud in a government healthcare program is described herein. The method includes registering a service provider with a healthcare provider and issuing a service provider identification code, registering at least one service of the service provider with the government sponsored healthcare provider and identifying a claim code for each registered service, issuing a code based on data from a biometric reading, a keypad entry with a PIN code, or an electronic signature pad entry to an individual related to a benefits program of the healthcare provider; using the code to determine if the individual is eligible for the healthcare program and performing three transmissions of information to reduce fraud in the systems.

14 Claims, 1 Drawing Sheet

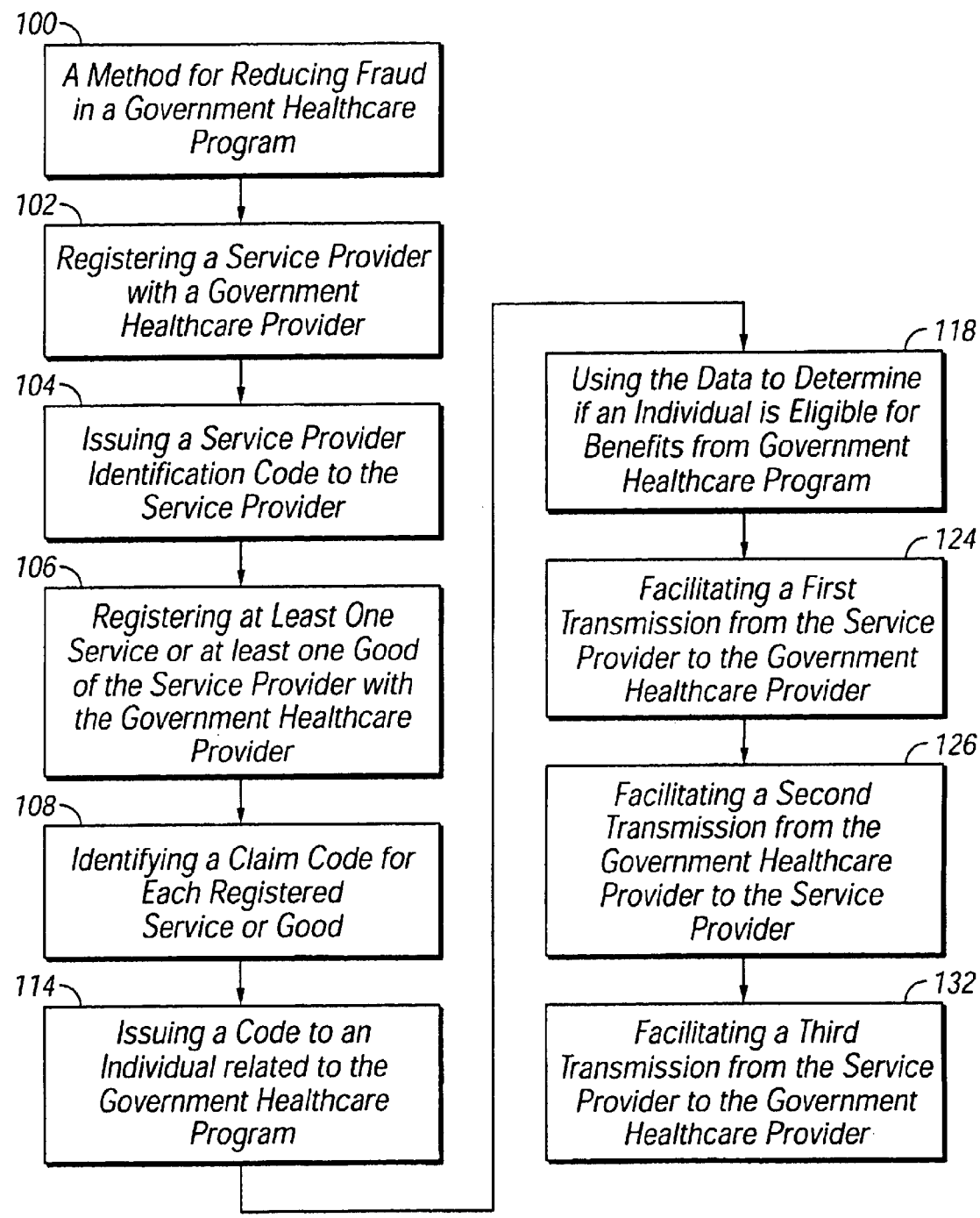

CARDLESS METHOD FOR REDUCING FRAUD IN GOVERNMENT HEALTHCARE PROGRAMS

CROSS-REFERENCE TO RELATED APPLICATIONS

This application is a continuation in part of co-pending U.S. patent application Ser. No. 10/428,609 filed May 2, 2003, which claims priority to provisional U.S. Patent Application Ser. No. 60/461,225 filed Apr. 8, 2003, and Ser. No. 60/461,226, filed Apr. 8, 2003 which is incorporated herein by reference.

Applicant hereby submits a Terminal Disclaimer in view of claims 1–19 of copending U.S. patent application Ser. No. 10/443,194. A draft of the Terminal Disclaimer was presented during the Interview on Mar. 30, 2004.

BACKGROUND

1. Field of Invention

Embodiments of the invention relate to reducing fraud in government healthcare programs that tracks identification, implements security measures, and other information to facilitate the transfer of funds and eliminate fraud in the benefit.

2. Description of Related Art

Providers of benefits from government sponsored healthcare providers have concerns wherein individuals can "double dip" into government sponsored healthcare provider programs getting twice the payment, or service providers could inadvertently "double bill" or inappropriately bill for services rendered.

In addition, problems have existed wherein proper service and goods providers for government healthcare programs have had to wait long periods of time to get paid for their services or goods rendered to the eligible employee. This situation has caused benefit costs to be very high, reducing overall benefits available due to these fraud issues.

A need has long existed for a system wherein the government sponsored healthcare provider advances funds to pay a service or goods provider so that an eligible individual does not have to handle money and the provider is promptly paid.

This need has been particularly great for incapacitated individuals such as those in nursing homes who are no longer able to handle funds or complicated transactions themselves.

A need exists for a method to reduce the magnitude of transaction costs involved in reviewing and adjudicating payment requests to a government sponsored healthcare provider that would have the effect of reducing the rate of increase of government sponsored healthcare provider benefit costs or enable more benefits to be provided to more people.

A need exists to reduce the traditionally high cost of benefit administration, including the review and adjudication of payment requests that result in service, goods or benefit providers having to act as "banks" or "credit sources" for individuals eligible for the benefit.

Methods and apparatus exist to streamline private sponsored insurance claim payment process, such as the method disclosed in U.S. Pat. No. 6,163,770. This patent reveals using a digital electrical apparatus to generate output for insurance documentation for a first insurance policy having a first risk and claims and reveal a concurrent second insurance policy for a second risk, wherein the second risk is different from the first. The processor of this method is connected to a memory device for storing and retrieving operations including machine-readable signals in the memory device, to an input device for receiving input data and converting the input data into input electrical data, to a visual display unit for converting output electrical data into output having a visual presentation, to a printer for converting the output electrical data into printed documentation, wherein the processor is programmed to control the apparatus to receive the input data and to produce the output data by steps including: inputting actuarial assumptions defining the first insurance policy and computing a value of a specific financial attribute of the first insurance policy; the method further including the step of inserting the value of the financial attribute in the first insurance policy and other printed documentation related to the first insurance policy. This method does not meet the needs identified above.

SUMMARY OF THE INVENTION

The present invention provides a cardless method for reducing fraud in government healthcare programs.

The method involves registering a service or goods provider with a government sponsored healthcare provider and issuing a service provider identification code to that provider. Services and goods of the provider can be registered with a healthcare provider and claim codes would correspond with each registered service. The healthcare provider can include a physician.

The method involves using a form of identification, such as fingerprints or retinal reading for individuals eligible for a government healthcare program. In addition to the biometrics reading, data from a keypad entry with a "PIN" code, or an electronic signature pad entry can be performed. The method involves a first identification check and then three transmissions between the service provider to the healthcare provider about proposed goods and services, information about the individual, and information about payment for the provider.

The invention is a method for reducing fraud in a government healthcare program. The method entails registering a service provider with a healthcare provider and issuing a service provider identification code and registering at least one service or at least one good of the service provider with the healthcare provider and identifying a claim code for each registered service or registered good.

The method involves three transmissions: a first transmission from the service provider to the healthcare provider (which includes the service provider identification code) the individual identification code, proposed product information for the individual, and proposed service information for the individual. The first transmission also contains corresponding claim codes for the proposed product, corresponding claim codes for the proposed service, a request to confirm the individual's eligibility for benefits under the government healthcare program, a validation that the proposed good or service is approved for the individual, the service provider's eligibility to render services or provide goods under the healthcare program, and a request to participate in an accelerated payment program for the proposed good or the proposed service.

The second transmission from the government sponsored healthcare provider to the service provider, wherein the second transmission comprises of: the individual's eligibility for benefits under the healthcare program; a validation that the proposed good or proposed service is approved for the individual; a validation of the service provider's eligibility to render services under the healthcare program; a confirmation that a payment program is available; and an authorization code to provide the proposed product and/or proposed service.

A third transmission is from the service provider to the government sponsored healthcare provider, and comprises of a list of claim codes for services rendered; acknowledgement by the individual that information on the product and/or service was provided to the individual; acknowledgement that the product or service has been received from the service provider; and a request for accelerated payment by the healthcare provider to the service provider.

BRIEF DESCRIPTION OF THE DRAWINGS

Aspects of the present invention will be described in greater detail with reference to the appended FIGURES.

FIG. 1 illustrates a diagrammatic representation of the overall method of embodiments of the invention.

DETAILED DESCRIPTION

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the pertinent art to make and use the inventions, when the information in this patent is combined with available information and technology. Various terms as used herein are defined below. To the extent a term used in a claim is not defined below, it should be given the broadest definition persons in the pertinent art have given that term as reflected in printed publications and issued patents.

The invention relates to a method for accelerating the providing funds to a service or goods provider from a government healthcare provider such as a federal, state or municipal healthcare provider.

This invention relates to the provision of a government sponsored sector benefit using a fingerprint reader, a retina reader, or similar biometric device.

The invention advantageously reduces fraud occurring in medical benefits by providing a safe method of pre-authorizing users for benefits prior to rendering the benefit.

The invention also advantageously prevents ineligible users from using services for which they are not authorized. The invention safeguards the government from users attempting to apply for the same service more than once, in other words "double dipping".

The first step of the method involves registering a service provider with a government healthcare provider and issuing a service provider identification code. The service provider identification code can then, optionally, be entered into an electronic retrieval system, wherein the electronic retrieval system comprises a database wherein the personal data is held for comparison purposes. The electronic retrieval system can include process, such as an internet query, an e-mail query, a network query, comparative information transfers and combinations thereof.

The method can further include creating a contractual relationship between the government healthcare provider and a third party for the benefit of the individual. The third party can be an insurance provider, such as a private insurance company.

Next at least one service or at least one good of the service provider is registered with the government healthcare provider and a claim code is issued which corresponds to each registered service or registered good.

Individuals are provided with an individual identification code that corresponds to a finger print or retina pattern.

A service provider has a biometrics reader. Once an individual's biometric is read, a first transmission from the service provider is made to the healthcare provider, wherein the first transmission is a service provider identification code (the individual identification code described above) and certain proposed information. Alternatively, a service provider can use a keypad which can receive a personal identification code "PIN" code or a device for receiving an electronic signature at the service providers.

Devices such an electronic signature pad manufactured by Welch Allyn model number TT3100 or a keypad for "PIN" entry manufactured by TRANZ model number 380 can be used.

The proposed information can be proposed product information for the individual; proposed service information for the individual; corresponding claim codes for the proposed product; and corresponding claim codes for the proposed service.

The first transmission preferably includes a request to confirm the individual's eligibility for benefits under the government healthcare program; a validation that the proposed good or service is approved for the individual; the service provider's eligibility to render services or provide goods under the government healthcare program; and a request to participate in an accelerated payment program for the proposed good or the proposed service. The first transmission can further include an indication of medical need from the service provider.

A second transmission is then made from the healthcare provider to the service provider. The second transmission includes the individual's eligibility for benefits under the government healthcare program, a validation that the proposed good or proposed service is approved for the individual, a validation of the service provider's eligibility to render services under the government healthcare program, a confirmation that payment, optionally accelerated payment, is available, and an authorization code to provide the proposed product and/or proposed service.

The smart card can facilitate a third transmission from the service provider to the government sponsored healthcare provider. The third transmission includes a list of claim codes for services rendered, an acknowledgement by the individual that information on the product and/or service was provided to the individual, an acknowledgement that the product or service has been received from the service provider, and a request for accelerated payment by the government sponsored healthcare provider to the service provider.

The biometric code enables access to and contains information on at least one or more of the following:

a. individual name (example—Richard Wood);
b. individual address (example—2396 Wood Street, Houston, Tex. 77019);

c. individual phone number (example—713-323-5555);
d. individual fax number (example—713-323-5554);
e. individual email address (example—Wood@aol.com);
f. government sponsored healthcare provider name and/or government sponsored sector administrator name (example—Mary Jones, Supervisor of the Food Stamp Program);
g. healthcare provider address;
h. healthcare provider phone number (example—281-873-8682);
i. healthcare provider fax number;
j. healthcare provider e-mail;
k. healthcare provider website;
l. healthcare provider claims representative;
m. type of benefit plan or plans;
n. individual benefit number (example—Group 200116289.);
o. individual group number or group plan number (example—KLINASD);
p. individual co-pay amount (example—$25);
q. individual benefit history;
r. instructions (example—benefits instructions embedded in the card);
s. other phone numbers;
t. issue date or "validity" date;
u. an expiration date or "expiry date";
v. statements as to ownership of the card;
w. statements as to eligibility of the individual on the plan to get benefits, and
x. disclaimers concerning use, misuse, and revocation of the benefits.

The accelerated fund payment schedule contemplated by this invention could be a 100% payment schedule or a partial accelerated fund payment schedule depending on the contract with the healthcare provider. It is contemplated that the funds would move electronically from the healthcare provider's bank account to the service provider's bank account, such as by wire transfer, or normal electronic banking procedures.

The biometric information is used to not only contain the information described above, but to initiate a link to the healthcare provider's database and between the healthcare provider's database and the service provider's database and the service provider's bank account. The information facilitates a first transmission from the service provider to the government healthcare provider. This first transmission can include information on:
  i. Determination if the individual is eligible;
  ii. determination that the service provider is authorized to provide the service;
  iii. proposed benefit costs;
  iv. information on benefit; and
  v. an acknowledgement that at least one benefit has been rendered from the service provider to the individual.

The first transmission can further include an indication of medical need for the service or good requested.

A second transmission from the government healthcare provider to the service provider occurs next. This second transmission can contain information on any amount of payment required by the individual. The amount of payment can be all or part of a co-payment fee, all or part of a deductible fee, and combinations of these fees.

A third transmission follows to the government healthcare provider from the service provider. This third transmission would include an acknowledgement that the amount of the co-payment and the deductible has been paid by the individual to the service provider thereby initiating payment by the government healthcare provider.

It should be noted that in the context of this invention, the healthcare provider is considered an entity that has been authorized by a federal or state government healthcare provider.

The method involves that on approximately the same day that the third transmission is received by the healthcare provider, or perhaps a few days later such as between 1 and 21 days, funds are then transmitted from the healthcare provider to the service provider for the benefit provided to the individual. This accelerated payment plan is a vast improvement over known systems that take up to eight months to pay a service provider.

This method contemplates that benefits can be a service related to a health procedure or eye glass prescriptions, dental examinations, dental procedures, mental health procedures, mental health therapies, physical therapy, podiatrists, doctor's visits, hospital visits, out-patient visits, food stamps, housing, or other benefits.

Now and with reference to the FIGURES, FIG. 1 shows a diagram of a method for reducing fraud in a government healthcare program 100.

First, a service provider is registered with a government healthcare provider (102) and the service provider is given an identification code (104). Next, at least one service or good of the service provider is registered with the government healthcare provider (106) and a claim code is given for the given registered service or good (108). An individual code is then issued for each individual related to the government healthcare program.

The data can then be used to determine if an individual is authorized for benefits of the government healthcare program (118). A biometric reader can be used. Again, alternatively to the biometric reader is a keypad onto which a PIN code can be typed or an electronic signature pad onto which the individual can sign their name for electronic transmission.

The biometrics, PIN or electronic signature data is used in a first transmission from the service provider to a program administrator (124) for a government healthcare provider.

A second transmission can then be facilitated from the government healthcare provider to the service provider (126). Additionally, a third transmission, as discussed above, can be facilitated from the service provider to the government healthcare provider (132).

While this invention has been described with emphasis on the preferred embodiments, it should be understood that within the scope of the appended the invention might be practiced other than as specifically described herein.

What is claimed is:

1. A method for reducing fraud in a government healthcare program consisting of:
  a. registering a service provider with a government healthcare provider and issuing a service provider identification code;
  b. registering at least one service or at least one good of the service provider with the government healthcare provider and identifying a claim code for each registered service or registered good;
  c. issuing and storing a first individual identification code to a first individual related to the government healthcare program, wherein the first individual identification code is linked to a biometric data of the first individual;

d. comparing second biometric data from a second individual against the first individual identification code to determine if the second individual is eligible for benefits from the government healthcare program;

e. facilitating a first transmission from the service provider to the government healthcare provider, wherein the first transmission comprises:
  i. the service provider identification code;
  ii. the individual identification code;
  iii. proposed information selected from the group consisting of proposed product information for the individual; proposed service information for the individual; corresponding claim codes for the proposed product; and corresponding claim codes for the proposed service;
  iv. an indication of medical need of the second individual; and
  v. a request to confirm:
    1. the second individual's eligibility for benefits under the healthcare program;
    2. a validation that the proposed good or service is approved for the second individual;
    3. the service provider's eligibility to render services or provide goods under the healthcare program; and
    4. a request to participate in an accelerated payment program for the proposed good or the proposed service;

f. facilitating a second transmission from the government healthcare provider to the service provider, wherein the second transmission comprises:
  i. the second individual's eligibility for benefits under the government healthcare program;
  ii. a validation that the proposed good or proposed service is approved for the individual;
  iii. a validation of the service provider's eligibility to render services under the government healthcare program;
  iv. a confirmation that an accelerated payment program is available;
  v. an authorization code to provide the proposed product and/or proposed service;

g. facilitating a third transmission from the service provider to the government healthcare provider, wherein the third transmission comprises:
  i. a claim codes list for services rendered;
  ii. acknowledgement by the second individual that information on the product and/or service was provided to the second individual;
  iii. acknowledgement that the product or service has been received from the service provider; and
  iv. a request for accelerated payment by the government healthcare provider to the service provider.

2. The method of claim 1, wherein the second transmission further comprises an alert to the service provider that a portion of the funds may need to come from the second individual and an indication of the amount of the funds.

3. The method of claim 1, wherein the third transmission further comprises dollar amount limits for the accelerated payment.

4. The method of claim 1, wherein the third transmission further comprises an acknowledgement that funds were collected from the second individual by the service provider.

5. The method of claim 1, further comprising the step of wherein between 1 and 21 days of receipt of the third transmission by the government healthcare provider funds are transmitted from the government healthcare provider to the service provider.

6. The method of claim 1, wherein the government healthcare program is a member of the group consisting of Medicare, Medicaid, state unemployment programs, state food stamp programs, school lunch programs, other federal health programs, government sponsored healthcare provider sponsored art and humanity programs, and social security programs.

7. The method of claim 1, wherein the first transmission further comprises a member of the group consisting of:
  a. a first transmission identification code;
  b. service provider information that comprises a member of the group consisting of:
    i. service provider code;
    ii. service provider name;
    iii. service provider address;
    iv. service provider office code; and
    v. service provider phone number;
  c. updated personal data; and
  d. individual information that comprises a member of the group consisting of:
    vi. individual name;
    vii. individual address;
    viii. government sponsored healthcare provider phone number;
    ix. individual social security number; and
    x. combinations thereof.

8. The method of claim 1, wherein the second transmission further comprises a member of the group consisting of:
  a. a notice as to further services or goods potentially needed by the individual;
  b. a depiction of the individual;
  c. an acknowledgement of the updated personal data; and
  d. a second transmission identification code and combinations thereof.

9. The method of claim 1, wherein the third transmission comprises of:
  a. a tracking number;
  b. a date on which the benefit was rendered;
  c. a total amount charged relative to the individual;
  d. a statement as to any amount that exceeds authorized service or good;
  e. detail on the claim codes for rendered service or good;
  f. a third transmission identification code; and
  g. combinations thereof.

10. The method of claim 1, wherein an individual's benefit history includes information on length of time on government sponsored healthcare provider programs and types of other government programs the individual is eligible to use.

11. The method of claim 1, further comprising creating a contractual relationship between the government healthcare provider and a third party for the benefit of the individual.

12. The method of claim 1, further comprising entering the service provider identification code into an electronic retrieval system.

13. The method of claim 12, wherein the electronic retrieval system comprises a process selected from the group consisting of an internet query, an e-mail query, a network query, comparative information transfers and combinations thereof.

14. The method of claim 1, wherein using second data to determine if a second individual is eligible for benefits comprises comparing first data to second data to obtain a verified identity.

* * * * *